United States Patent [19]

Christiansen

[11] 4,408,341
[45] Oct. 4, 1983

[54] X-RAY EXAMINATION APPARATUS HAVING A MOVABLE X-RAY SOURCE

[75] Inventor: Dieter Christiansen, Schönberg, Fed. Rep. of Germany

[73] Assignee: U.S. Philips Corporation, New York, N.Y.

[21] Appl. No.: 320,359

[22] Filed: Nov. 12, 1981

Related U.S. Application Data

[63] Continuation of Ser. No. 127,713, Mar. 6, 1980, abandoned.

[30] Foreign Application Priority Data

Mar. 7, 1979 [DE] Fed. Rep. of Germany ....... 2908914

[51] Int. Cl.³ .................................. G03B 41/16
[52] U.S. Cl. ..................... 378/196; 378/209
[58] Field of Search .............. 378/196, 195, 209; 369/322, 328

[56] References Cited

U.S. PATENT DOCUMENTS

| | | | |
|---|---|---|---|
| 2,680,199 | 6/1954 | Abel | 378/27 |
| 3,708,664 | 1/1973 | Bock | 378/196 |
| 3,838,286 | 9/1974 | Prendergast | 378/196 |

*Primary Examiner*—Craig E. Church
*Attorney, Agent, or Firm*—Marc D. Schechter

[57] ABSTRACT

The invention relates to an X-ray examination apparatus comprising a frame and a patient examination table which is slidably connected to the frame. This apparatus is particularly suitable for making Bucky exposures. The apparatus offers the advantage that it is very accessible from the sides, without mounting the guide rail (the guide rail supports the stand which supports the X-ray source) on the wall or the ceiling. To this end, a column which supports the X-ray source is movable in a longitudinal direction along a guide rail. The guide rail, in turn, is movable in the longitudinal direction on a carriage. The carriage, in turn, is movable in the longitudinal direction on a stationary frame. This results in a telescopic movement of the movable parts and in a displacement range which is larger than the width of the frame.

7 Claims, 7 Drawing Figures

X-RAY EXAMINATION APPARATUS HAVING A MOVABLE X-RAY SOURCE

This is a continuation of application Ser. No. 127,713, filed Mar. 6, 1980, now abandoned.

BACKGROUND OF THE INVENTION

The invention relates to X-ray examination equipment made up of a frame, a patient examination table which is slidably connected to the frame, and a column which supports an X-ray source. The column is movable on a guide rail which extends in a longitudinal direction.

Equipment of this kind is very suitable for making exposures. In such apparatus, the X-ray source and X-ray film (arranged in the frame) remain aligned with respect to each other in a central position, while the floating table top supporting the patient is moved. For this method of making exposures, it is important that the frame has small dimensions in the longitudinal direction. This is to enable the radiologist to walk right up to the frame from the head end or foot end when the table top has been shifted to the foot end or head end, respectively. A further requirement to be satisfied by such X-ray apparatus is that the X-ray source must be slidable over a comparatively long distance in the longitudinal direction, beyond the basic frame. For example, this enables exposures to be made by means of a cut-film changer situated at the head or foot end.

A Bucky exposure apparatus of the kind described above is known from U.S. Pat. No. 3,838,286. The guide rail for guiding the column in this apparatus is arranged at the longitudinal side of the patient examination table and its length exceeds that of the frame of the patient examination table. The guide system thus projects beyond both ends of the frame and is arranged to be stationary in the room. This apparatus has the drawback that walking around the apparatus and working on the patient at the foot end and the head end, and particularly at the longitudinal side where the guide system is arranged, are severely restricted or even precluded, because the area of the feet and the knees is blocked over the entire length of the table.

SUMMARY OF THE INVENTION

An object of the invention is to provide an X-ray apparatus which is suitable for making Bucky exposures which comprises a short and narrow frame, which offers a large displacement range for the column, and which permits the radiologist to approach the apparatus from the side on which the guide rail is present.

In an X-ray apparatus according to the invention, this object is achieved in accordance with the invention the guide rail is movable in the longitudinal direction on a carriage. This carriage is also movable in the longitudinal direction along a stationary frame. The carriage, the guide rail and the column are linked so that when the carriage is moved relative to the frame, the guide rail is moved in the same direction over twice the distance, and the column is moved in the same direction as the carriage over three times the distance relative to the frame.

In a device of this kind, the dimensions of the guide system, consisting of the carriage, the guide rail and the frame, need not be larger than the frame of the patient examination table which supports the table top. This is so even though the column can be displaced beyond the frame in the longitudinal direction.

In sliding the column, the individual parts of the guide system move in a telescopic manner with respect to each other. In other words, in sliding the column the carriage is displaced (over a part of the displacement distance) with respect to the stationary frame, the guide rail is displaced with respect to the carriage, and the column with the X-ray source is displaced with respect to the guide rail. All these displacements are in the same direction so that they are added, with the result that the overall displacement of the column can exceed the dimensions of the guide system in its collapsed state. Thus, a very compact construction is obtained and a part of the longitudinal side where the guide system is situated is freely accessible to the physician.

The movable parts of the apparatus according to the invention could in principle run on rollers or rails on the floor. However, there would then be the danger that the feet of the radiologist or other examiner could run over by the moving part of the apparatus. Therefore, in a preferred form of the invention at least one roller, which is connected to the carriage, is arranged between the guide rail and the frame so that when the guide rail is displaced, the roller is forced to roll on the frame. This roller is rotatable around a horizontal axis and it carries the weight of the guide rail which, in turn, carries the weight of the column which is displaceable thereon.

Thus, in this preferred form of the invention, only the (stationary) frame contacts the floor. The moving parts are each supported by the neighboring moving part in the direction of the patient examination table. The roller with the horizontal axis has two functions; (a) it supports the guide rail and hence the weight of the column carried thereby, and (b) it also ensures that when the guide rail is displaced, the carriage travels over half the distance traveled by the guide rail. This latter function is ensured because the guide rail rolls on top of this roller which, in turn, rolls on the frame. Thus, the carriage is moved over half the distance as the guide rail in the direction of displacement.

BRIEF DESCRIPTION OF THE DRAWING

The invention will be described in detail hereinafter with reference to the accompanying diagrammatic drawing.

DESCRIPTION OF THE PREFERRED EMBODIMENTS

Figure 1:
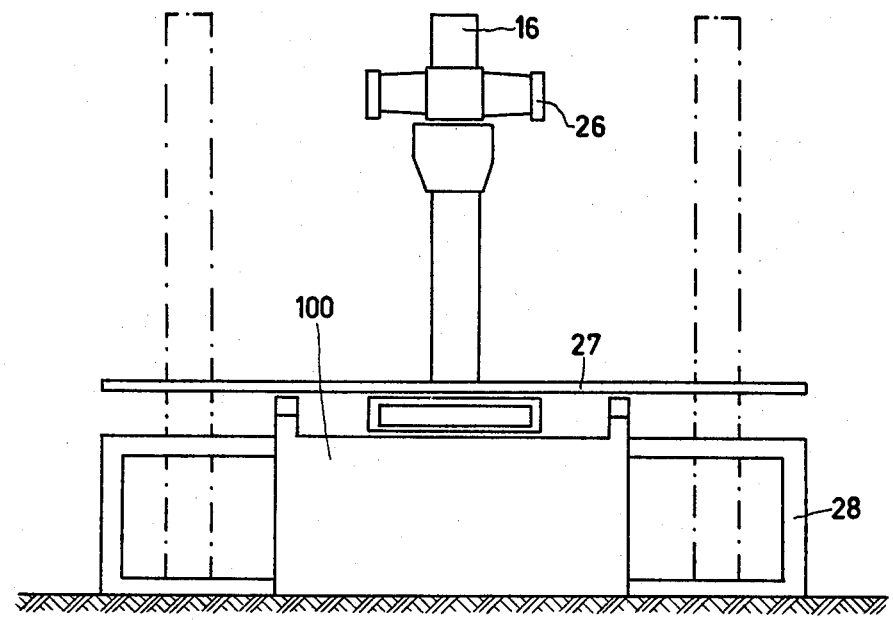
FIG. 1 shows a known apparatus from U.S. Pat. No. 3,838,286.

The reference numeral 27 in FIG. 1 denotes the patient examination table which is arranged on a basic frame. Behind the table there is arranged a column 16 which supports and X-ray source 26. A multi-leaf collimator is rigidly arranged below the source 26. Utilizing a frame-like guide device 28, the X-ray source can be moved in the longitudinal direction from the central position (shown) to an extreme lateral position at the head end or the foot end of the table (denoted by dash/-dot lines). The frame impedes free access to the table top from the longitudinal side on which it is arranged, even during examinations where the X-ray source is in the central position and the slidability of the X-ray source is not even utilized.

Figure 2:
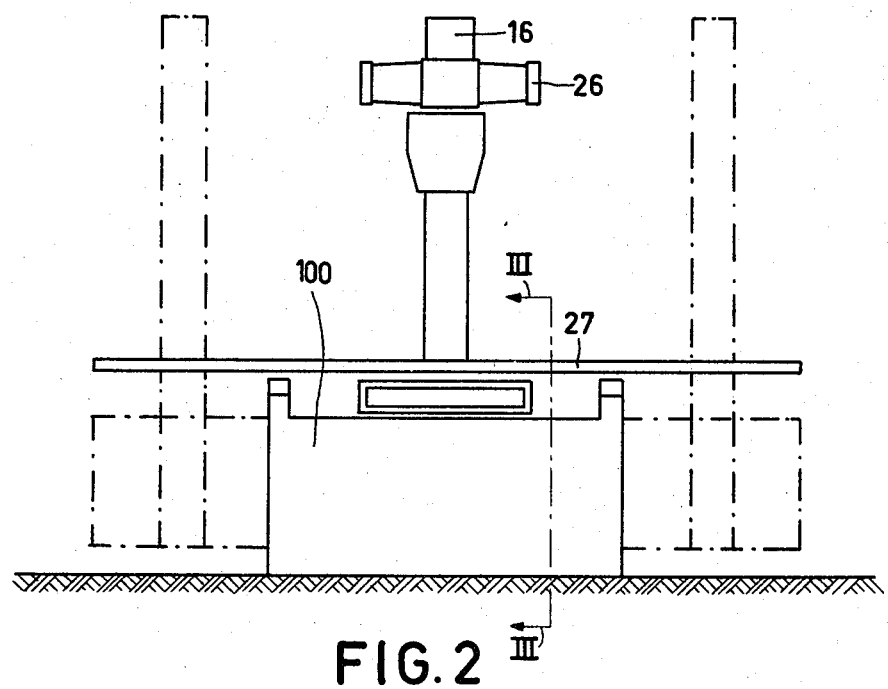
FIG. 2 shows an apparatus according to the invention.

The apparatus according to the invention, which is shown in FIG. 2, differs from known apparatus in that the guide device does not project laterally beyond the frame of the patient examination table 7 and does not impede the access to the head end or foot end of the table top when the guide device is in its center position.

However, the column 16 with the X-ray source 26 can be displaced to the foot end or to the head end, as denoted by dash/dot lines. In this case the guide system is also displaced to the foot or head end, but it is not on the floor. Consequently the examiner still has enough room for his feet when working with the inventive apparatus.

Figure 3:
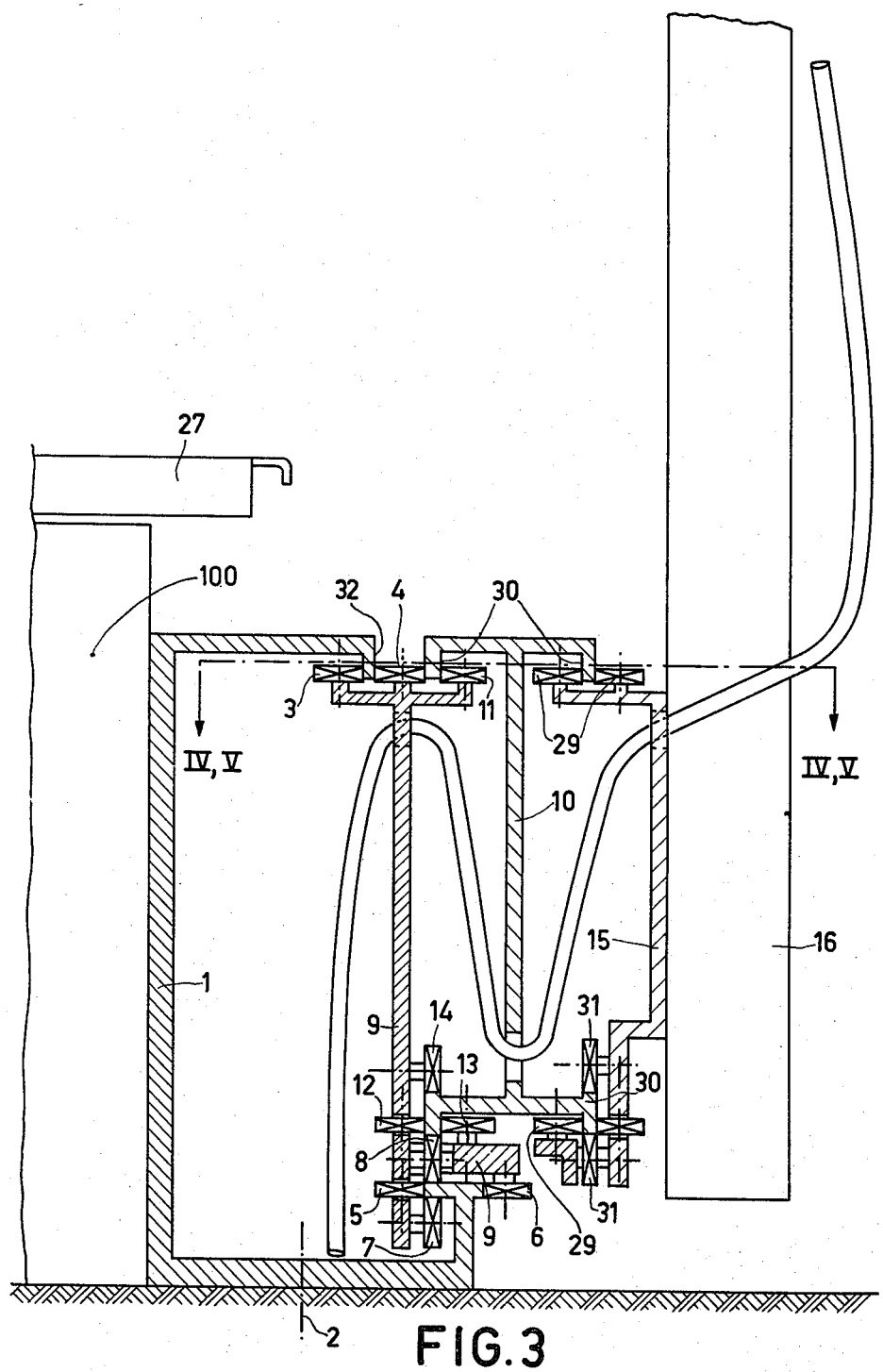
FIG. 3 is a cross-sectional view along line III—III of FIG. 2.

FIG. 3 shows the guide device in a plane perpendicular to the longitudinal direction. The column 16 is connected to an auxiliary carriage 15 which can be displaced on a guide rail 10 in the longitudinal direction. The auxiliary carriage 15, being essentially a flat-iron frame, is provided at its top and bottom with roller pairs 29 having vertical axes of rotation. The roller pairs run vertical on side faces of flanges 30 of the guide rail 10. The side faces extend perpendicular to the plane of the drawing.

Rollers 31, having horizontal axes of rotation which are situated in the plane of the drawing, are also connected to the auxiliary carriage 15. The rollers 31 run on horizontal end faces on the flange 30, so that the weight of the auxiliary carriage 15 and the column 16 is supported by the guide rail 10. Because the column 16 is supported completely by the guide rail 10, it need not run on the floor. Therefore, it can terminate from 10 to 20 cm above the floor.

The guide rail 10, having a double-T cross-section with perpendicular flanges 30 over its entire length (in the direction to the plane of the drawing), bears on the running faces of rollers 8 having a horizontal axis of rotation. Only one of these rollers 8 is shown in the drawing (the other roller is situated behind the one shown, outside the plane of the drawing). The axes of rotation of the rollers 8 are parallel to the plane of the drawing.

The roller 8 run on a frame 1 which is connected to the floor (at 2) and to the patient examination table. This frame thus supports the guide rail 10 and hence the auxiliary carriage 15, the column 16 and the X-ray source 26.

The rollers 8 are connected to a carriage 9 whose construction is similar to that of the auxiliary carriage 15. At the top, carriage 9 comprises three roller pairs end rollers 3 and 11, and central rollers 4. All of these rollers have vertical axes of rotation. These rollers are spaced apart with enough space for the flanges 32 and 30 which are connected to the frame 1 and the guide rail 10, respextively. As a result, there is a set distance between the frame 1 and the guide rail 10.

On the lower part of the carriage 9 there are also provided roller pairs 5 and 6, and 12 and 13 with vertical axes of rotation. These rollers run on corresponding side faces on the frame 1 or the guide rail 10. The lateral distance between all components of the guide device, including the column 16, is thus constant.

Also provided are further rollers 14 and 7 whose axes of rotation extend parallel to the axes of rotation of the rollers 8 and which are connected to the carriage 9 above and below the roller 8, respectively. Between these rollers and the rollers 8 extends a part of the guide rail 10 or the frame 1, so that the positions of the individual elements of the guide device are also defined vertically. The elements, therefore, can move with respect to each other only in the direction perpendicular to the plane of the drawing.

Figure 4:
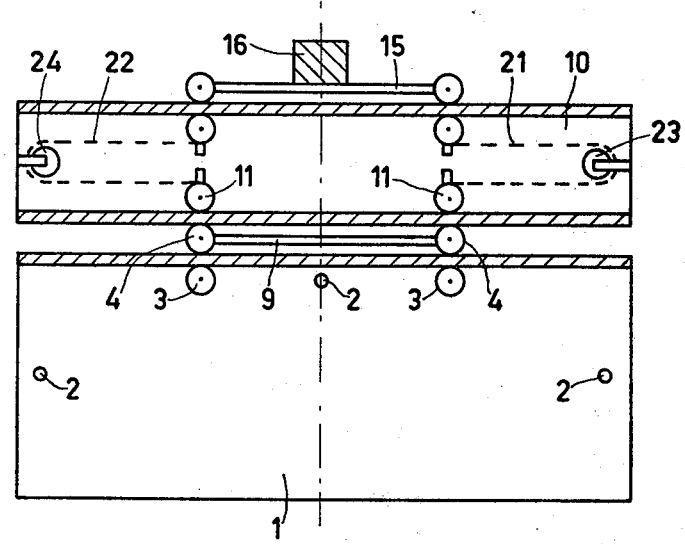
FIGS. 4 and 5 are a cross-sectional views of FIG. 3 on line IV,V—IV,V.
Figure 5:
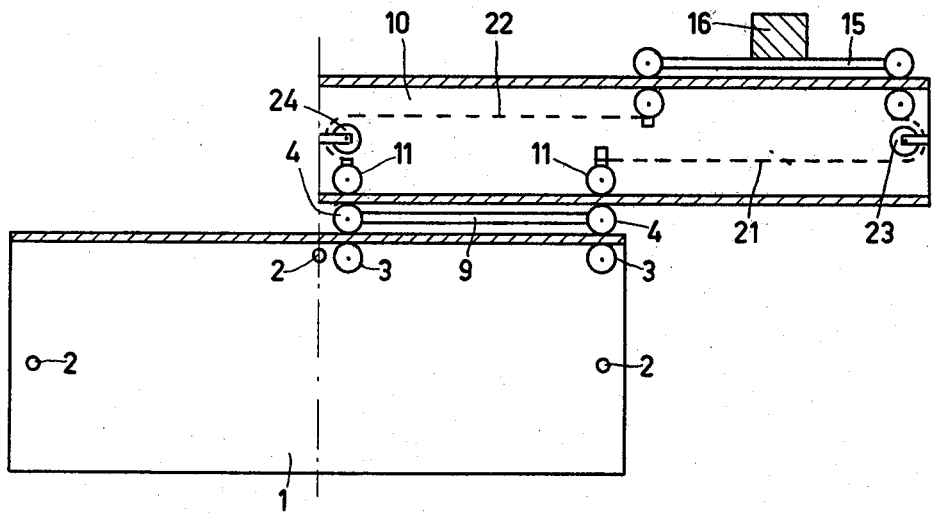

As shown in FIGS. 4 and 5, guide pulleys 23 and 24 are provided at the head and foot ends of the guide rail 10. Around the guide pulleys 23 and 24 there are ropes, steel belts, or similar parts 21 and 22 (the group of useable parts being referred to as "cord means"). The ends of ropes 21 and 22 are connected to the carriages 15 and 9. It is thus ensured that the auxiliary carriage 9 and carriage 15 can move only in opposite directions with respect to the guide rail 10, each carriage travelling the same distance.

When the column is displaced, for example, to the right, the following happens:

The carriage 9 is displaced over a distance a with respect to the frame 1 (this distance is arbitrary for the time being). A displacement of this kind is possible only when the rollers 4 and the rollers 8 roll on the running faces of the frame 1. This is possible only if the guide rail 10 is shifted to the right over exactly twice the distance of the carriage 9, that is to say over the distance 2a.

The carriage 9 is thus displaced to the left over the distance a with respect to the guide rail 10. For the reasons stated above, the auxiliary carriage 15, which is connected to carriage 9 via the guide pulleys 23 and 24 and the belts 21 and 22, is displaced with respect to the guide rail over the same distance a but to the right. The overall displacement of the auxiliary carriage 15 or the column 16 then results from an addition of the displacements of the guide rail 10 (2a) and the auxiliary carriage 15 with respect to the guide rail 10 (a). In other words, the overall displacement of the column 16 to the right amounts to 3a, which is three times the displacement of the carriage 9.

Thus, during this movement the column 16 and the auxiliary carriage 15 are displaced with respect to the guide rail 10. At the same time, the guide rail 10 is displaced with respect to the carriage 9, and the carriage 9 is displaced with respect to the frame 1. Each displacement is over the same distance a. The forced coupling between the movement of the individual units is ensured by the rollers 8, which support the weight of the guide rail 10, the carriage 15 and the column with the X-ray source 26, because the frictional forces occurring due to such loading of the rollers are so large that, without rolling of the rollers 8 on the frame 1 and rolling of the guide rail 10 on the rollers in the same direction but over twice the distance, movement of the carriage 9 with respect to the frame 1 is virtually impossible. Therefore, it is substantially impossible for the auxiliary carriage 15 to be displaced with respect to the guide rail 10, or for the guide rail 10 to be displaced with respect to the carriage 9, while all other parts maintain their positions. Therefore, all parts always return to the same starting position (FIG. 4).

Preferably, the length of the guide rail 10 is exactly equal to that of the frame 1, for example, 1 meter. The length of the carriage 9 is preferably exactly equal to that of the auxiliary carriage 15, both being half the length of the guide rail 10 or the frame 1, e.g. 50 cm. All parts then simultaneously reach their extreme positions on the parts on which they are moved. The maximum displacement distance in a direction then amounts to three times half the length of the carriage 75 cm. If the frame is 1 meter wide, the extreme positions of the column 16 are then situated 1.50 meter apart.

As is shown in FIG. 4, the column 16 is mounted at the center of the auxiliary carriage 15. The carriage 15 is mounted at the center of the guide rail 10, the guide rail 10 is mounted at the center of the carriage 9, and the carriage 9 is mounted at the center of the frame 1. As a result of this symmetrically centered arrangement, the displacement in both directions is symmetrical. However, an asymmetrical arrangement is also feasible. Such an arrangement would produce an asymmetrical displacement so that the column can be displaced further in one direction than in the opposite direction.

The displacement of the two carriages 9 and 15 in opposite directions with respect to the guide rail 10 can also be realized in a manner other than that shown in FIGS. 4 and 5 by means of the guide pulleys 23 and 24 and the belts or ropes or similar 21 and 22. For example, a toothed rod, extending in the direction of displacement, could be connected to each carriage, the rods cooperating with one or more gearwheels connected to the guide rail 10. By suitable stepping up or down, the movements in opposite directions need not have the ratio 1:1.

Figure 6:
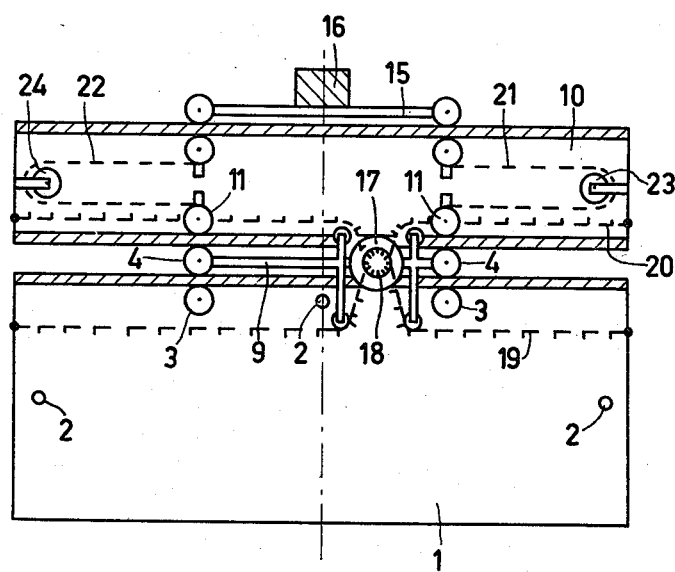
FIGS. 6 and 7 are cross-sectional views corresponding to the FIGS. 4 and 5, but with motor drives.
Figure 7:
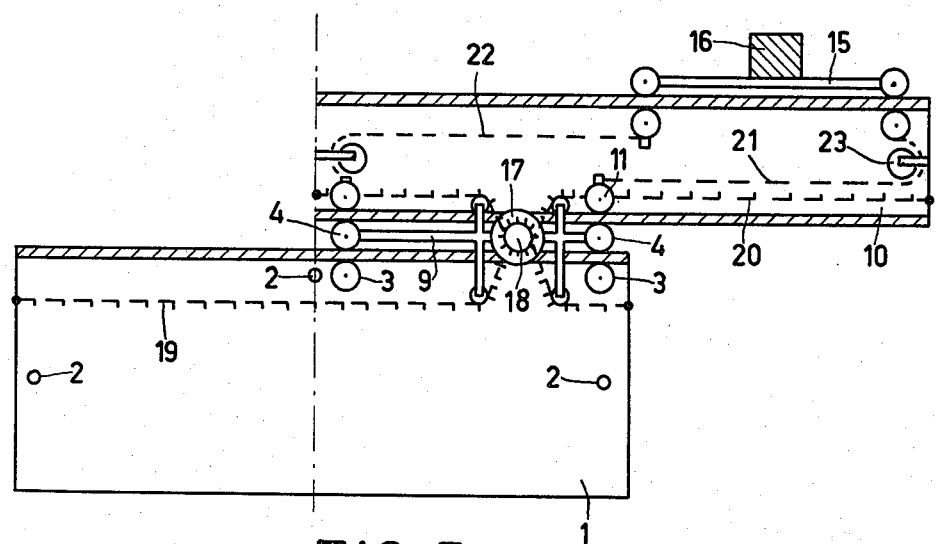

The coupling of the carriage 9 to the guide rail 10, ensuring that the carriage and the guide rail move at a ratio of 1:2 with respect to the frame 1, can also be realized in a manner other than by means of the rollers 8 and 4. For example, guide pulleys with ropes or toothed rods and gearwheels or lever action can be used. FIGS. 6 and 7 show a further possibility for obtaining this movement behavior. These figures are based on the use of a motor drive.

At the opposing ends (in the longitudinal direction) of the frame 1 as well as of the guide rail 10, there are secured toothed belts 19 and 20, respectively. Each of the toothed belts 19 and 20 are guided in opposite directions around a toothed wheel (the drawing shows only the front toothed wheel 18) which are arranged on a common shaft which extends perpendicular to the plane of the drawing and which are driven by a motor 17. When the toothed wheels 18 are driven counterclockwise, the motor 17 pulls itself and the carriage 9 on which it is mounted to the right, and hence it also pulls the guide rail 10. As a result of the rotation of the toothed wheel 18, which is coupled to the toothed belt 20, the guide rail 10 is shifted further to the right; it travels twice the distance of the carriage 9 with respect to the frame 1. The carriages 9 and 15 are coupled in the same way as in the FIGS. 4 and 5.

FIG. 7 shows the arrangement in the extreme right position.

What is claimed is:

1. X-ray examination apparatus comprising:
   a frame;
   a patient examination table, slidably connected to the frame;
   a guide rail extending in a longitudinal direction;
   a column, movable on the guide rail in the longitudinal direction; and
   an X-ray source on the column;
   characterized in that the apparatus further comprises:
   a carriage, movable on the frame in the longitudinal direction, the guide rail being movable on the carriage in the longitudinal direction; and
   linkage means for assuring that when the carriage, the guide rail, or the column are moved relative to the frame, the guide rail is moved in the same direction as the carriage but at twice the distance relative to the frame, and the column is moved in the same direction as the carriage but at three times the distance relative to the frame.

2. X-ray examination apparatus as claimed in claim 1, characterized in that the linkage means comprises at least one roller connected to the carriage, said guide rail bearing on the roller so that when the guide rail is moved relative to the frame, the guide rail rolls on the roller and the roller is forced to roll on the frame.

3. X-ray examination apparatus as claimed in claim 2, characterized in that the roller is rotatable around a horizontal axis, the roller supports the weight of the guide rail, and said guide rail supports the weight of the column.

4. X-ray examination apparatus as claimed in claim 3, characterized in that:
   the frame has a flange extending in a vertical plane parallel to the longitudinal direction;
   the guide rail has a flange extending in a vertical plane parallel to the longitudinal direction; and
   the linkage means further comprises two end rollers and a central roller rotatable around vertical axes, said rollers connected to the carriage, one end roller and the central roller bearing on the frame flange, the other end roller and the central roller bearing on the guide rail flange, so that when the guide rail is moved relative to the frame, the guide rail rolls on the central roller and the central roller is forced to roll on the frame.

5. X-ray examination apparatus as claimed in claim 4, characterized in that the linkage means further comprises:
   two guide pulleys connected to the guide rail, said pulleys being displaced along the longitudinal direction with respect to each other;
   first cord means passed around one guide pulley, said cord means having one end fastened to the carriage and the other end fastened to the column;
   second cord means passed around the other guide pulley, said cord means having one end fastened to the carriage and the other end fastened to the column.

6. X-ray examination apparatus as claimed in claim 5, characterized in that the linkage means further comprises:
   first belt means having two ends each fastened to the frame at positions displaced in the longitudinal direction;
   second belt means having two ends each fastened to the guide rail at positions displaced in the longitudinal direction; and
   a motor coupled to each belt means.

7. X-ray examination apparatus as claimed in claim 6, characterized in that:
   the guide rail and the frame have substantially the same length in the longitudinal direction;
   the column is attached to an auxiliary carriage which is movable on the guide rail in the longitudinal direction; and
   the two carriages have lengths in the longitudinal direction which are approximately one-half the lengths of the guide rail and frame.

* * * * *